United States Patent [19]
Arensdorf et al.

[11] Patent Number: 5,676,641
[45] Date of Patent: Oct. 14, 1997

[54] STABILIZED ANKLE SUPPORT

[76] Inventors: Stephen C. Arensdorf, 3711 Thunderbird Dr.; Lawrence Thompson Stromgren, 3005 Tam O'Shanter, both of Hays, Kans. 67601

[21] Appl. No.: 223,453

[22] Filed: Apr. 5, 1994

Related U.S. Application Data

[63] Continuation-in-part of Ser. No. 171,028, Dec. 21, 1993, abandoned, which is a continuation of Ser. No. 48,369, Apr. 15, 1993, abandoned.

[51] Int. Cl.⁶ .................................................. A61F 5/00
[52] U.S. Cl. ........................ 602/27; 602/26; 602/29
[58] Field of Search ........................... 602/27, 28, 29, 602/60, 61, 63, 65

[56] References Cited

U.S. PATENT DOCUMENTS

| | | | |
|---|---|---|---|
| 3,674,023 | 7/1972 | Mann | 602/65 |
| 4,166,460 | 9/1979 | Applegate | 602/27 |
| 4,367,733 | 1/1983 | Stromgren | 602/27 |
| 4,844,058 | 7/1989 | Vogelbach | 602/27 |
| 4,962,768 | 10/1990 | Stromgren et al. | 602/27 |

*Primary Examiner*—Richard J. Apley
*Assistant Examiner*—Beverly M. Flanagan

[57] ABSTRACT

A reusable ankle support for stabilizing the ankle region comprises a sock-like elastic sheath provided with longitudinally inflexible, medial and lateral reinforcing elements, a pair of crossed, elongated elastic strap members attached to the bottom of the sheath and a guide fastener on the front top of the sheath. After the sheath is positioned on the foot of the wearer, the strap members are wrapped around the ankle in a predetermined manner over the sheath and reinforcing elements. The guide fastener engages a portion of at least one strap so as to provide a desired tension thereto. The strap configuration is such that a pair of stirrups are presented which are limited in elasticity by stretch locks. Once applied to the ankle, the longitudinal inflexibility of the reinforcing elements and the stirrup-lock system and the uplifting support of the stirrups provide medial and lateral rigidity to restrain the ankle from rolling to the outside or inside.

10 Claims, 3 Drawing Sheets

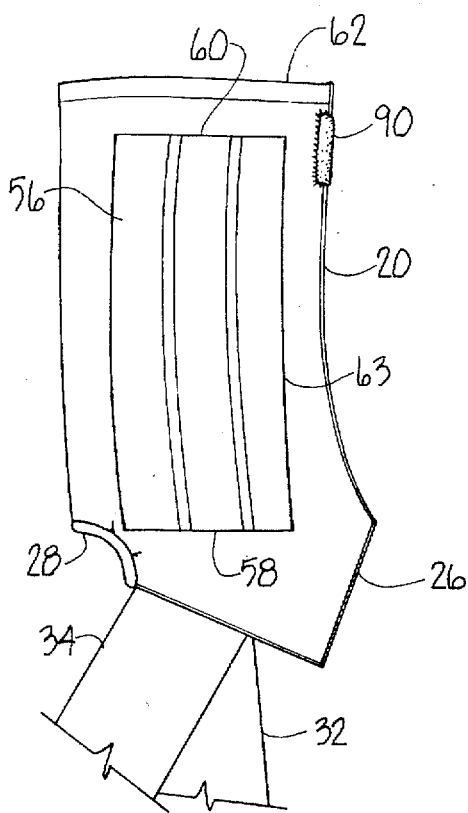
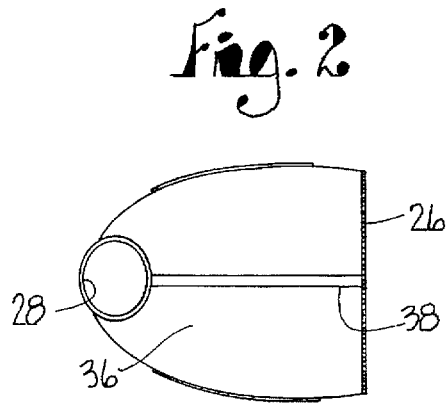
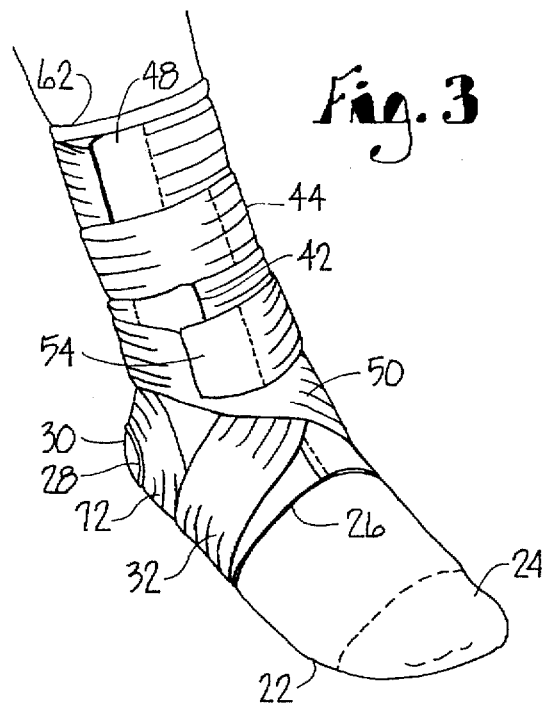

STABILIZED ANKLE SUPPORT

CROSS REFERENCE TO RELATED APPLICATIONS

This application is a continuation-in-part of application Ser. No. 08/171,028, filed Dec. 21, 1993, now abandoned, which is a continuation of application Ser. No. 08/048,369, filed Apr. 15, 1993, now abandoned.

BACKGROUND OF THE INVENTION

This invention relates to improvements in ankle supports and, in particular, to a support which presents structure for insuring a desired lift to the ankle as well as rigidity to the medial and lateral sides of the ankle by providing a combination of medial and lateral braces and a fastener/guide for directing a desired wrapping of a stirrup lock.

Ankle supports or wraps and taping of the ankle are commonly used to prevent or reduce the severity of debilitating ankle sprains. Athletes in both contact and noncontact sports are particularly susceptible to this injury. Methods of wrapping include using adhesive tape strapping or reusable canvass-type ankle wraps, either of which is applied to virtually immobilize the contact between the bones and the ligaments of the ankle region in order to prevent injurious pulling, stretching or tearing of these ligaments.

Adhesive tapes, however, can be expensive to use, both because they are not reusable and because of the manpower costs involved in properly taping or supervising the taping of an ankle of an athlete. Furthermore, tape has a tendency to loosen during use. In recent years the utilization of reusable ankle wraps or supports has proved to be a solution to these problems, an example being the stirrup-lock ankle support disclosed in U.S. Pat. No. 4,962,768 owned by the assignee hereof. The stirrup-lock support enhances the stability of both the medial and lateral sides of the ankle joint and provides protection against low sprains, i.e., injuries to ligaments below the lateral malleolus of the fibula and the medial malleolus of the tibia, often referred to as the "ankle bones."

Although the stirrup-lock support has proven to be effective, the stirrups are located alongside and below the ankle bones and thus do not provide maximum stabilization above the ankle bones at the lower leg. The most common sprain is an inversion where the ankle rolls to the outside (or laterally) while the foot remains in the medial position. The reverse can also occur, an eversion when the ankle rolls to the inside (medially) and the foot remains in a lateral position. To provide maximum protection against the occurrence of either condition, the ankle should be supported both above and below the lateral and medial malleolus. However, in some cases the wrap may be wound about the foot such that the resulting stirrup may not have the proper tension therein and may not provide the desired stabilizing action and/or "lift" to the ankle. Such a condition may occur when portions of the wrap are adjacent or low on the ankle instead of displaced therefrom. This is particularly true on the lateral side of the ankle so as to address the more common "inversion" sprain. Thus, it is desirable to provide a means for assuring at least the lateral or outside stirrup lock is wrapped in a proper position relative to the ankle so as to provide an optimal tension therein and a resulting uplifting support to the ankle.

SUMMARY OF THE INVENTION

It is, therefore, the primary object of the present invention to provide a reusable ankle support which provides a sufficient uplifting support and medial and lateral rigidity to restrain the ankle from rolling to the outside or inside.

As a corollary to the foregoing object, it is an important aim of the present invention to provide such a support employing a combination of side braces and stirrup supports to impart the requisite rigidity to the medial and lateral sides of the ankle.

A still further object of the present invention, as aforesaid, is to provide means for guiding the ankle support into a desired position about the ankle so as to provide and maintain a desired uplifting support to the ankle particularly at the lateral side thereof.

Another object of the invention is to provide an ankle support which is an improvement upon the stirrup-lock ankle support disclosed in the above-identified patent, by providing reinforcing elements on the medial and lateral sides of the foot-receiving sheath of the support which cooperate with the stirrup configuration to present without discomfort to the wearer an effective brace along the sides of the entire ankle region against which the ankle is forced in an inversion or an eversion.

Still another important object of the invention is to provide bracing elements as aforesaid which comprise medial and lateral strips of material that are essentially inflexible in directions longitudinally of the leg, and which are held in place by the strap members of the support that are drawn around the sheath and over the elements when the support is applied to the wearer.

Yet another important object of this invention is to provide bracing elements as aforesaid which, though longitudinally inflexible, have transverse two-way stretchability in order to yield with the foot-receiving sheath and conform to the configuration of the wearer's ankle.

Another important object of this invention, as aforesaid, is to provide a fastener element on the front of the foot-receiving sheath for mating with a portion of a strap member so as to guide a strap member into a desired stirrup-lock position.

Other objects and advantages of this invention will become apparent from the following description taken in connection with the accompanying drawings, wherein is set forth by way of illustration and example, an embodiment of this invention.

DESCRIPTION OF THE DRAWINGS

FIG. 1 is a side view of the ankle support before application to a wearer, the straps being broken away to fully reveal one of the reinforcing elements.

FIG. 2 is a bottom plan view of the ankle support as it would appear on the foot (not shown) of the wearer.

FIG. 3 shows the support applied to the right ankle and illustrates the foot in a position which could cause an inversion.

FIG. 6 is a perspective view similar to FIG. 5 showing the sock-like sheath slipped over the wearer's foot with the rear outside portion of one strap member being drawn into an operative position and atop a guide fastener located on the front of the sheath.

FIG. 7 is a similar perspective view and showing the front outside portion of the strap member being drawn into an operative position about the previously positioned strap.

FIG. 8 is a similar view showing the outside portions of both strap members in place and the rear inside portion of the rear strap member being drawn into its operative position.

FIG. 9 is a final view similar to FIGS. 6 through 8 showing the ankle support with the front inside portion of one strap member being drawn into its operative position about the previously positioned strap portion.

DETAILED DESCRIPTION

Figure 4:
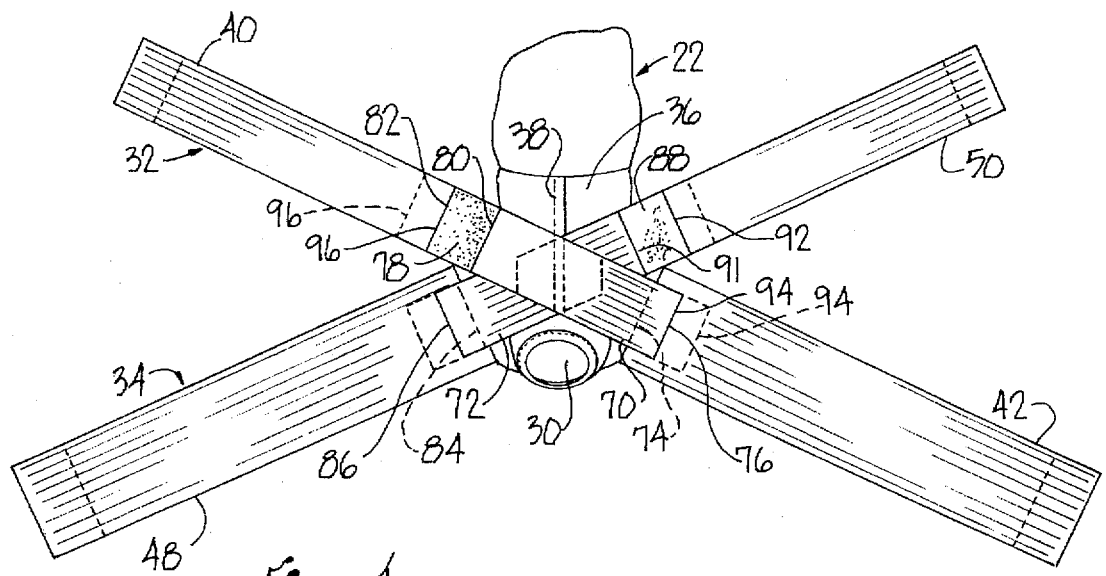
FIG. 4 is a bottom plan view of the ankle support shown on the right foot of the wearer with neither of the strap members in their operative positions. The broken lines depict the degree of stretch which can be achieved from the stirrup portions.

A tubular, sock-like elastic sheath 20 receives the foot 22 and lower leg of a wearer as is clear in the drawings, the sheath 20 being slipped over the foot 22 which preferably has an athletic sock 24 thereon. The sheath 20 has a front opening 26 from which the toes of the foot 22 extend, and a heel opening 28 through which the heel 30 of the foot protrudes. The sheath 20 is made from an elastic fabric such as SPANDEX® or the like, and is sized to have an unstretched diameter somewhat less than the wearer's leg so that the fabric is stretched as it is pulled over the foot 22 into position. The preferred material has four-way stretchability, meaning that it has resilience in directions up and down the leg as well circumferentially. This holds the sheath 20 in place and also imparts some support to the ankle region.

Two elongated elastic strap members 32 and 34 are crossed under the bottom portion 36 of the sheath 20 and anchored at the intersection thereof by stitching the members to a seam 38 at the bottom of the sheath 20. The strap members 32 and 34 are longitudinally stretchable and are placed in tension as they are drawn into their respective operative positions illustrated by the sequence depicted in FIGS. 6–9. The opposed ends 40 and 42 of strap member 32 are provided with corresponding fasteners 44 and 46 which are adapted to mate with the material comprising strap member 32, fasteners 44 and 46 being preferably composed of VELCRO® hook material. Likewise, opposed ends 48 and 50 of strap member 34 are provided with respective VELCRO® fasteners 52 and 54 which are adapted to mate with the material of member 34 upon pressure contact therewith.

Figure 5:
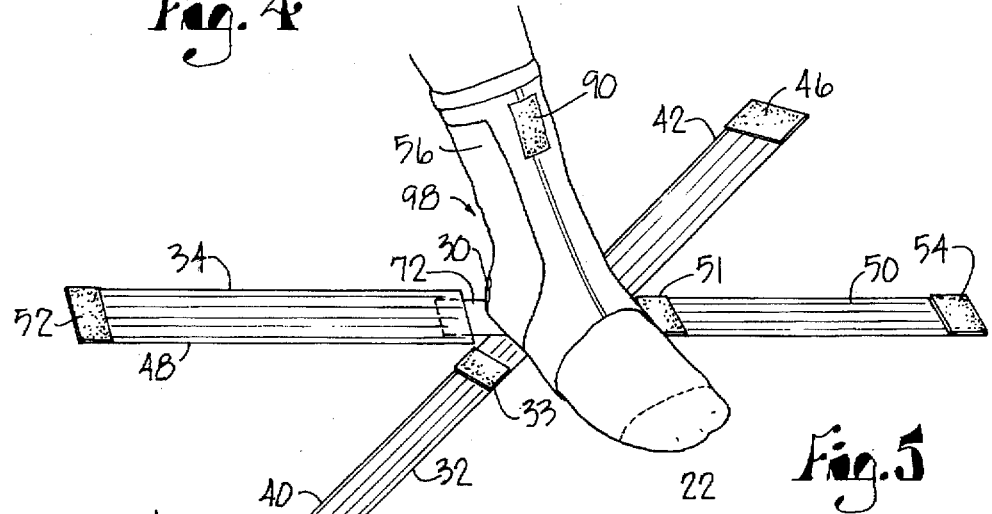
FIG. 5 is a perspective view taken from the outside of the right foot and shows the ankle support on the ankle of the wearer with neither of the strap members in operative positions.
Figure 6:
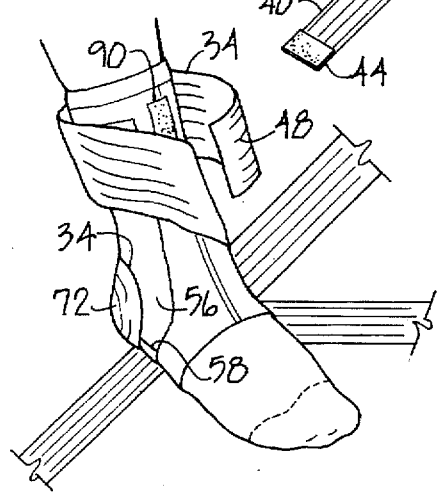
FIGS. 6 through 9 show, in order, the steps of wrapping the ankle as follows.

FIG. 5 shows the ankle support of the present invention prior to drawing the strap members 32 and 34 into their operative positions and, therefore, reveals an elongated reinforcing element 56 overlying the lateral side of the sheath 20. The element 56 is a strip of material of sufficient width to cover the lateral malleolus, typically approximately 5.5 centimeters, and has a lower end 58 (FIG. 2) terminating in spaced relationship to bottom seam 38 and an upper end 60 positioned adjacent the normally upper end 62 of the tubular sheath 20. The reinforcing element comprising strip 56 is secured to the sheath 20 by stitching 63 at its side and end edges (FIG. 1), and is made from a fabric composed of a blend of nylon and lycra woven to provide a two-way stretch transversely of the strip 56, i.e., in directions circumferentially around the wearer's leg. The material is purposely woven to preclude any substantial flexibility longitudinally of strip 56 so that the material does not yield in response to forces that would tend to place the strip in longitudinal tension.

Similarly, a substantially longitudinally inflexible reinforcing element is provided on the medial side of the sheath 20 by a like strip of material 64 (FIG. 11) extending from its lower end 66 upwardly along the medial side of sheath 20 to its upper end 68 adjacent the upper end 62 of sheath 20. It should particularly be noted in FIG. 2 that the lower ends 58 and 66 of the strips 56 and 64 terminate at the bottom portion 36 of the sheath 20 in spaced relationship to each other, equidistant from the bottom seam 38. As best shown in FIG. 1, it is preferred that the bottom ends 58, 66 of elements 56, 64 are displaced from the bottom of the sheath and generally toward the top of the heel opening 28 (i.e., about 4 centimeters) so that the ends 58, 66 will not interfere with the lower portion of the user's foot during use. The two strips 56 and 64, therefore, do not present a continuous stirrup and thus permit the bottom portion 36 of the sheath 20 to freely yield under the wearer's foot in response to normal movement. The relief provided by the spaced lower ends 58 and 66 is particularly important in running in order to prevent a cutting effect on the foot which could occur as the foot repeatedly strikes the ground.

The strap members 32 and 34 are of identical construction and have central stirrup portions 70 and 72, respectively, attached by stitching to the seam 38. Stirrup portion 70 terminates at corresponding stretch locks, one of which comprises parallel transverse lines of stitching 74 and 76 adjacent one end thereof forming a joint at which stirrup portion 70 is attached to the wider, outer segment of strap member 32 that presents end 42. The other stretch lock is provided by an inelastic spacer 78 located adjacent the other end of stirrup portion 70 and secured thereto by parallel transverse lines of stitching 80 and 82. The inelastic spacer 78 is a rectangular piece of nonstretchable material. Likewise, the stirrup portion 72 has corresponding stretch locks comprising similarly situated inelastic components, i.e., parallel transverse lines of stitching 84 and 86 forming a joint, and an inelastic spacer 88 that is secured to strap member 34 by parallel transverse lines of stitching 91 and 92.

The stirrup portions 70 and 72 are made from an elastic material having a relatively low stretch factor, preferably approximately 30 percent. The respective inelastic stretch locks serve to isolate these stirrup portions or segments 70 and 72 from the outer segments of strap members 32 and 34 and thus enable the stretch to be pulled from the stirrup segments 70 and 72 when force is applied to the strap members 32 and 34 as they are placed in operative positions. The phantom lines in FIG. 4 show the amount of stretch which may be achieved from the stirrup segment 70 when the terminal end 94 of stirrup segment 70 is displaced as shown. Likewise, the terminal end 96 of spacer 78 can be displaced to the maximum shown by the phantom lines. The maximum amount of stretch which may be achieved from stirrup segment 72 is similarly shown by phantom lines.

Figure 7:
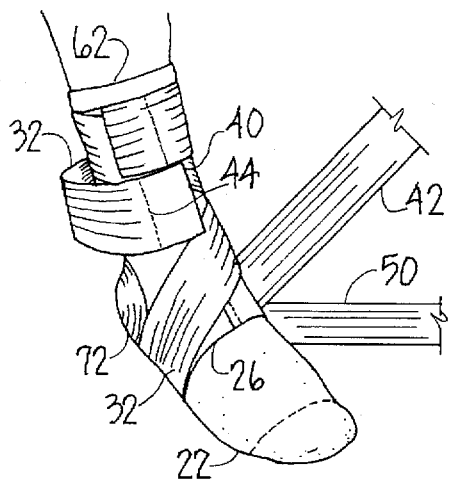

In use, the sheath 20 is slipped over the ankle of the wearer as described above. The manner of wrapping the ankle support is depicted in FIGS. 5–9. Initially, strap members 32 and 34 extend outwardly from the sheath 20 in an X-shaped configuration (FIG. 5). End 48 of the rear outside portion of strap member 34 is drawn behind the ankle region 98, then around the front of the ankle, and about the guide fastener 90 on the front of the sheath 20. This relationship produces a tension in the strap and provides a desired uplifting support by the formed stirrup 72 crossing the heel 30. Moreover, the engagement of the guide fastener 90 with the strap 34 causes an enhanced coverage of stirrup 72 with heel 30. This enhanced support and/or strap tension arises as the strap is directed towards the top of sheath 20 and in a wrapping relationship high about the foot. Thus, fastener 90 also acts as a guide to the user to provide such uplifting support by stirrup 72. Fastener 52 then mates with the strap 84 material to thereby secure this outer strap segment in its operative position about the top 62 of sheath 20 as seen in FIG. 7. As shown in FIG. 7 end 40 of the front outside portion of strap member 32 is drawn in front of the ankle region 98 (across the tibia) and to the rear thereof. It is then drawn across the fibula to the front of the ankle region 98 where fasteners 33, 44 mate with the underlying strap 32 material the end 40 being operatively positioned above the lateral malleolus of the fibula. It is here noted, as shown in FIG. 7, that the strap member 40 encompasses the previously wrapped strap 34 so as to maintain the previous wrap and resulting lateral heel lock in place. This wrapping positions the strap segments above and below the lateral malleolus 100.

Figure 8:
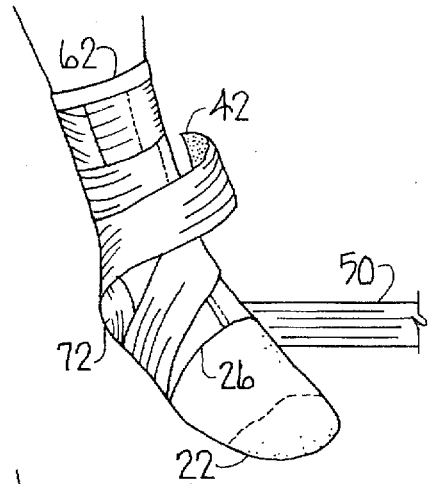
Figure 9:
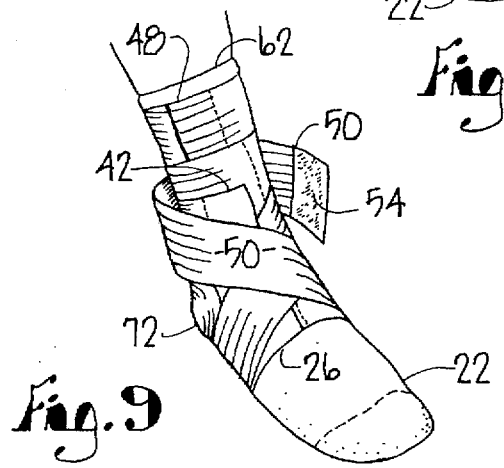

As shown in FIG. 8, the opposed inside rear end 42 of strap member 32 is then placed into operative position by drawing it behind the ankle 98 to present stirrup 70 and across the fibula to the front of the ankle and then around as shown in FIG. 8 to complete the wrap, end 42 being secured on the lateral side of the support by fastener 46 engaging the underlying strap material. Finally, as shown in FIG. 9 end 50 of strap member 34 is drawn in front of the ankle, across the fibula, and to the rear thereof. End 50 is then drawn across the tibia to the front of the ankle where fasteners 51, 54 mate with the underlying strap material (FIG. 8).

Figure 10:
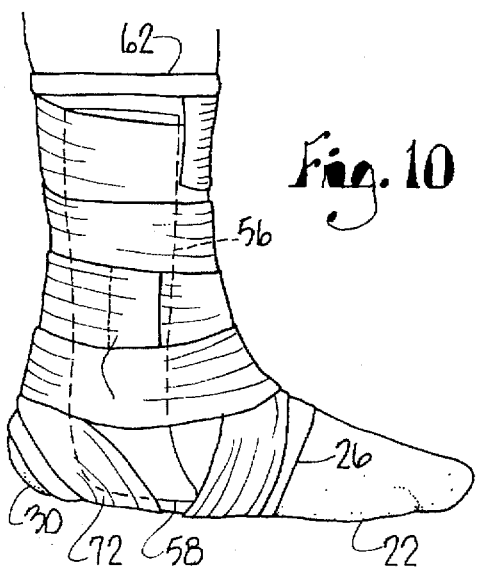
FIG. 10 is an elevational view taken from the outside of the right foot showing the ankle support in a fully secured position on the right foot of the wearer with the underlying lateral reinforcing element being shown in phantom lines.
Figure 11:
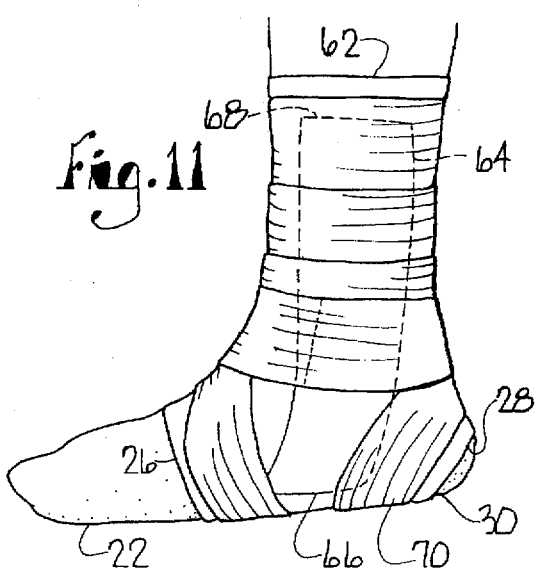
FIG. 11 is an elevational view as in FIG. 10 but taken from the inside of the right foot, showing the opposed lateral reinforcing element in phantom lines.

Upon conclusion of the wrapping, as shown in FIGS. 10 and 11, the wearer is provided with an uplifting ankle support having medial and lateral sides braced by the longitudinally inflexible reinforcing strips 56 and 64 which are held firmly against the ankle by the wrapped strap members 32 and 34. Furthermore, the wrapped straps provide the crossed stirrups 70 and 72 to further enhance the stability that is achieved. The bracing strips 56 and 64 provide medial and lateral rigidity to restrain the ankle from rolling to the outside or inside, and the V-shaped configuration formed by the stirrup segments 70 and 72 below the lateral malleolus 100 and the medial malleolus 102 augments the protective action of the reinforcing strips at the base of the ankle region to prevent low sprains.

It is appreciated that the above-described guide fastener 90 causes the lateral stirrup 72 to be directed towards the top 62 of the sheath 20 with a resulting tension in the strap 72. This relationship provides a desired uplifting support to the stirrup 72. Moreover, the initial stirrup 72 is locked into position by the remaining wraps of straps. Such stirrup 72 delimits the more common inversion of the foot leading to ankle sprain. Furthermore, the stretch locks for stirrup segments 70 and 72 enable the stretch to be pulled from the stirrups as the strap members 32 and 34 are drawn into their operative positions, thereby limiting the elasticity of the stirrup segments and causing them to become substantially longitudinally inflexible when the strap members are drawn into their operative positions over the sheath 20 and reinforcing strips 56 and 64. These relationships impart stability to the ankle region by the action of two support components provided by the present invention, the longitudinally inflexible medial and lateral reinforcing strips, the guide fastener 90 and the resulting enhanced stirrup-lock mechanism.

Although the ankle support is described for use with the right foot, it is understood that it may be interchangeably used with the left foot without any modifications. The manner of wrapping is simply reversed. Accordingly, the ankle support can be used for either foot with identical accompanying advantages and results.

It is to be understood that while certain forms of this invention have been illustrated and described, it is not limited thereto except insofar as such limitations are included in the following claims.

Having thus described the invention, what is claimed as new and desired to be secured by Letters Patent is:

1. An ankle support comprising:

a tubular, sock-like elastic sheath having a normal upper end and adapted to be slipped over either ankle of a wearer and, when worn, to extend upwardly therefrom over the lower leg to said upper end, a pair of elongated, substantially longitudinally inflexible and transversely flexible and stretchable reinforcing elements on medial and lateral sides respectively of said sheath extending from beneath the ankle bone of a wearer to a position adjacent said end, a pair of elongated elastic strap members each having opposed first and second end portions, means anchoring each of said strap members intermediate its end portions to said sheath on a bottom portion thereof adapted for disposition underneath the foot of a wearer, said strap members in use being drawn around said sheath over said elements into operative positions, crossing each other below the ankle bone of the wearer, and said members in their operative positions presenting stirrup portions adjacent said anchoring means for supporting both the medial and lateral sides of the ankle, fastener means on respective end portions of said strap members for securing the same in said operative positions, and means associated with said stirrup portions for limiting the elasticity thereof to cause said stirrup portions to become substantially longitudinally inflexible when said strap members are drawn around the ankle into their operative positions over said elements, whereby the reinforcing elements and stirrup portions provide medial and lateral rigidity to restrain the ankle from rolling to the outside or inside.

2. The ankle support as claimed in claim 1, wherein said elements have respective lower ends terminating at said bottom portion of the sheath in spaced relationship to each other, whereby said bottom portion can freely yield in response to the action of the wearer's foot.

3. The ankle support as claimed in claim 1, wherein each of said elements comprises a substantially longitudinally inflexible strip of material secured to the corresponding side of said sheath and having transverse stretchability to thereby provide protective rigidity but yield with said sheath to conform to the ankle configuration of the wearer.

4. The ankle support as claimed in claim 3, wherein said strips have respective lower ends terminating at said bottom portion of the sheath in spaced relationship to each other, whereby said bottom portion can freely yield in response to the action of the wearer's foot.

5. The ankle support as claimed in claim 3, further comprising stitching joining said strips with said sheath on respective medial and lateral sides thereof to secure the strips to the sheath.

6. The ankle support as claimed in claim 3, wherein each of said strips has a transverse dimension sufficient to cover the ankle bone of a wearer.

7. An ankle support comprising:

a tubular, sock-like elastic sheath having a normal upper end and adapted to be slipped over either ankle of a wearer and, when worn, to extend upwardly therefrom over the lower leg to said upper end, a pair of elongated, substantially longitudinally inflexible and transversely flexible and stretchable reinforcing elements on medial and lateral sides respectively of said sheath extending from beneath the ankle bone of a wearer to a position adjacent said end, a pair of crossed, elongated elastic strap members each having opposed first and second end portions, each of said strap members comprising a pair of outer segments presenting said first and second end portions respectively, an intermediate stirrup segment and stretch locking means interconnecting said outer segments with said intermediate stirrup segment, means anchoring each of said crossed strap members intermediate said stirrup segment thereof to said sheath on a bottom portion thereof adapted for disposition underneath the foot of a wearer, said strap members in use being drawn around said sheath over said elements into operative positions, crossing each other below the ankle bone of the wearer, and said members and stirrup segments in their operative positions presenting an essentially V-shaped configuration for supporting both the medial and lateral sides of the ankle to restrict both medial and lateral movement thereof, fastener means on respective end portions of said strap members for securing the same in said operative positions, and said stretch locking means isolating said stirrup segments from said outer segments and limiting the elasticity of said stirrup segments to cause said stirrup segments to become substantially longitudinally inflexible when said strap members are drawn around the ankle into their operative positions over said elements, whereby the reinforcing elements and stirrup segments provide medial and lateral rigidity to restrain the ankle from rolling to the outside or inside.

8. The ankle support as claimed in claim 7, wherein said elements have respective lower ends terminating at said bottom portion of the sheath in spaced relationship to each other, whereby said bottom portion can freely yield in response to the action of the wearer's foot.

9. An ankle support comprising:

a tubular, sock-like elastic sheath having a normally upper end and adapted to be slipped over either ankle of a wearer and, when worn, to extend upwardly therefrom over the lower leg to said upper end, a pair of elongated, substantially longitudinally inflexible and transversely flexible and stretchable reinforcing elements on medial and lateral sides respectively of said sheath extending from beneath the ankle bone of a wearer to a position adjacent said end, a pair of elongated elastic strap members each having opposed first and second end portions, means anchoring each of said strap members intermediate its end portions to said sheath on a bottom portion thereof adapted for disposition underneath the foot of a wearer, said strap members in use being drawn around said sheath over said elements into operative positions, crossing each other below the ankle bone of the wearer, and said members in their operative positions presenting stirrup portions adjacent said anchoring means for supporting both the medial and lateral sides of the ankle, guide means along said upper end of said sheath for matching with a portion of one of said strap members while being drawn in said operative position, said guide means mating said one strip member into a desired operative position presenting said stirrup position, fastener means on respective end portions of said strap members for securing the same in said operative positions, and means associated with said stirrup portions for limiting the elasticity thereof to cause said stirrup portions to become substantially longitudinally inflexible when said strap members are drawn around the ankle into their operative positions over said elements, whereby the reinforcing elements and stirrup portions provide medial and lateral rigidity to restrain the ankle from rolling to the outside or inside.

10. The ankle support as claimed in claim 9 wherein said guide means comprises a fastener for a mating engagement with said portion of one of said strap members.

* * * * *

UNITED STATES PATENT AND TRADEMARK OFFICE
CERTIFICATE OF CORRECTION

PATENT NO.    : 5,676,641
DATED         : October 14, 1997
INVENTOR(S)   : Stephen C. Arensdorf; Lawrence Thompson Stromgren It is certified that error appears in the above-identified patent and that said Letters Patent is hereby corrected as shown below:

In Claim 9, column 8, line 4, delete "normally" and insert --normal-- therein.

Signed and Sealed this

Seventeenth Day of February, 1998

Attest:

Attesting Officer

BRUCE LEHMAN

Commissioner of Patents and Trademarks